United States Patent
Yi et al.

(10) Patent No.: US 8,345,322 B2
(45) Date of Patent: Jan. 1, 2013

(54) SCANNING APPARATUS HAVING DUAL POWER MODE

(75) Inventors: Tsu-hsun Yi, Taipei (TW); Mi-lai Tsai, Keelung (TW)

(73) Assignee: Genesys Logic, Inc., Shindian (TW)

( * ) Notice: Subject to any disclaimer, the term of this patent is extended or adjusted under 35 U.S.C. 154(b) by 748 days.

(21) Appl. No.: 12/546,887

(22) Filed: Aug. 25, 2009

(65) Prior Publication Data
US 2010/0296134 A1    Nov. 25, 2010

(30) Foreign Application Priority Data

May 19, 2009   (TW) ................................ 98208697 U

(51) Int. Cl.
*H04N 1/04* (2006.01)
*H04N 1/32* (2006.01)

(52) U.S. Cl. ........ 358/474; 358/471; 358/486; 358/442; 358/468

(58) Field of Classification Search ........................ None
See application file for complete search history.

(56) References Cited

U.S. PATENT DOCUMENTS

| | | | | |
|---|---|---|---|---|
| 6,002,508 A | * | 12/1999 | Mai | 359/212.1 |
| 6,031,636 A | * | 2/2000 | Chen | 358/442 |
| 6,357,011 B2 | * | 3/2002 | Gilbert | 713/300 |
| 6,963,429 B2 | * | 11/2005 | Suzuki et al. | 358/474 |
| 6,995,877 B2 | * | 2/2006 | Suzuki | 358/474 |
| 7,441,127 B2 | * | 10/2008 | Sugasawa | 713/300 |
| 8,018,607 B2 | * | 9/2011 | Nuttall et al. | 358/1.14 |
| 8,193,663 B2 | * | 6/2012 | Sato | 307/87 |
| 2002/0015174 A1 | * | 2/2002 | Nanpei | 358/1.14 |

* cited by examiner

*Primary Examiner* — Cheukfan Lee

(57) ABSTRACT

A scanning apparatus having dual power mode is described. The scanning apparatus includes a detection module, a switch unit, and a power controller. The detection module detects a first voltage signal and a second voltage signal for generating a detecting signal. The switch unit receives the commands from the power controller for outputting the first voltage signal and/or the second voltage signal to the image acquiring device of the scanning apparatus. The power controller determines whether the first voltage signal is detected according to the detecting signal. While the first voltage signal is detected, the power controller controls the switch unit to output the first voltage signal and/or the second voltage signal to the image acquiring device. While the first voltage signal is not exist, the power controller controls the switch unit to output the second voltage signal to the image acquiring device.

15 Claims, 2 Drawing Sheets

SCANNING APPARATUS HAVING DUAL POWER MODE

CLAIM OF PRIORITY

This application claims priority to Taiwanese Patent Application No. 098208697 filed on May 19, 2009.

FIELD OF THE INVENTION

The present invention relates to a scanning apparatus, and more particularly relates to a scanning apparatus having a dual power mode apparatus for supplying either a universal serial bus (USB) power or an external power source to the scanning apparatus, or supplying both the universal serial bus (USB) power and the external power source to the scanning apparatus.

BACKGROUND OF THE INVENTION

With the rapid development of information technology, electrical document are widely used. However, for the purpose of storage, processing and delivery via internet network of the documents, it is necessary to scan the paper document into the format of electrical documents. Currently, the scanner is supplied with the power from the universal serial bus (USB) of the computer or with the proper voltage level which is generated by the conversion of the mains supply via an external adaptor. These two kinds of powers supply are determined while the scanner is designed, which is in an invariable status. Moreover, when the scanner is electrically connected to the computer for use, the power supply mode of the scanner is identified by the computer. However, the above-mentioned ways have restriction and inconvenience. When the scanner is supplied with the power from USB signal, the power supply ability of USB is lower, resulting in decreasing the operation speed of the scanner. When the scanner is supplied with the proper voltage level which is generated by the conversion of the mains supply via an external adaptor, the portability of the scanner is downgraded and it is necessary to find the power socket of the mains supply disadvantageously. Consequently, there is a need to improve the conventional scanner to solve the aforementioned problems.

SUMMARY OF THE INVENTION

One objective of the present invention is to provide a scanning apparatus having a dual power mode apparatus for supplying either a universal serial bus (USB) power or an external power source to the scanning apparatus, or supplying both the universal serial bus (USB) power and the external power source to the scanning apparatus.

According to the above objective, the present invention sets forth a scanning apparatus having a dual power mode apparatus. The scanning apparatus includes a dual power mode apparatus and an image acquiring device. The dual power mode apparatus includes a detection module, a switch unit, and a power controller. The image acquiring device includes a light source, an image sensor, a voltage control unit and a driving motor.

While the dual power mode apparatus is operated, the detection module receives the first voltage signal and the second voltage signal, or only receives the second voltage signal. The detection module then detects the levels of the first voltage signal and the second voltage signal respectively for generating a detecting signal. The switch unit switches the first voltage signal and the second voltage signal for selection. The power controller receives the detecting signal and the universal serial bus (USB) signal, wherein the universal serial bus (USB) signal further comprises a control signal, data signal and the second voltage signal. The power controller determines whether the first voltage signal is detected according to the detecting signal. The power controller controls the switch unit to activate the switch unit to output the first voltage signal for driving an image acquiring device when the first voltage signal is detected. In another case, the power controller controls the switch unit to activate the switch unit to output the first voltage signal and the second voltage signal for driving the image acquiring device when the first voltage signal is detected. The switch unit outputs the second voltage signal for driving the image acquiring device when the power controller determines that the first voltage signal does not exist. In one embodiment, the computer system controls the power controller so that the power controller is capable of determining whether the first voltage signal is detected according to the detecting signal. Meanwhile, the power controller is used to report the detecting signal to the computer system and sends the control signal from the computer system to switch unit.

The detection module further continuously detects the status of the first voltage signal. The dual power mode apparatus determines whether the power controller has a control entitlement of the first voltage signal when the status of the first voltage signal is changed. The power controller controls the switch unit to output the first voltage signal, or output the first voltage signal and the second voltage signal to the image acquiring device when the status of the first voltage signal is not changed.

When the power controller has a control entitlement of the first voltage signal, the power controller is capable of enabling the control entitlement of the first voltage signal. In another case, when the power controller has no the control entitlement of the first voltage signal, the power controller is disabled from the control entitlement of the first voltage signal.

When the control entitlement of the first voltage signal is enabled, the power controller determines whether the universal serial bus (USB) signal is disconnected from the scanning apparatus. The power controller transmits a re-connection request to allow a computer system to enumerate the scanning apparatus when the power controller disconnects the universal serial bus (USB) signal from the scanning apparatus. The scanning apparatus reports the status of the first voltage signal to the computer system via the power controller. The detection module further continuously detects the status of the first voltage signal when the power controller does not disconnect the universal serial bus (USB) signal from the scanning apparatus. The control entitlement of the first voltage signal for the power controller is disabled and the power controller reports the status of the first voltage signal to the computer system when the power controller has no the control entitlement of the first voltage signal.

Specifically, when the power controller determines whether the universal serial bus (USB) signal is disconnected and makes re-connection according to the status of the first voltage signal, an application program operated in the computer system can be utilized to enable or disable the power controller. When the power controller enables the control entitlement of the first voltage signal, the power controller disconnects the universal serial bus (USB) signal from the scanning apparatus, and the power controller reports the status of the first voltage signal when the computer system re-enumerate the scanning apparatus. When the power controller disables the control entitlement of the first voltage signal, the power controller reports the changed status of the first voltage signal to the computer system.

In another embodiment, the power controller processes the control signal from the computer system for disconnecting the universal serial bus (USB) signal to enumerate the scanning apparatus. Basically, the disconnection step is used to meet the command from the computer system but not associated with the control status of the first voltage signal. Therefore, when the power controller is disabled from the control entitlement of the first voltage signal and the power controller cannot disconnect the universal serial bus (USB) signal from the scanning apparatus. However, the application program in the computer system can control the power controller to perform the disconnection step.

According to the above-mentioned, the present invention provides a scanning apparatus having a dual power mode apparatus for supplying either a universal serial bus (USB) power or an external power source to the scanning apparatus, or supplying both the universal serial bus (USB) power and the external power source to the scanning apparatus. Therefore, the scanning apparatus having a dual power mode apparatus is supplied with the universal serial bus (USB) power and/or the external power source for increasing the portability of the scanner and improving the inconvenience due to the lack of power socket mains supply.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein.

DETAILED DESCRIPTION OF THE PREFERRED EMBODIMENTS

Figure 1:
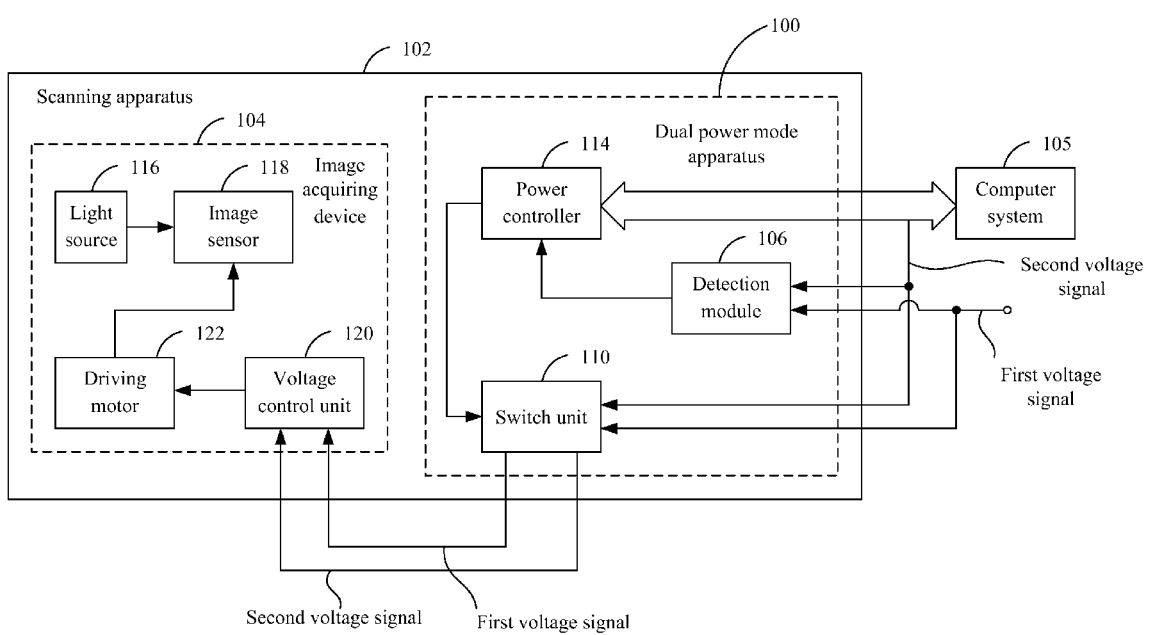
FIG. 1 is a schematic block diagram of a scanning apparatus having dual power mode according to one embodiment of the present invention.

FIG. 1 is a schematic block diagram of a scanning apparatus 102 having a dual power mode apparatus 100 according to one embodiment of the present invention. The scanning apparatus 102 includes a dual power mode apparatus 100 and an image acquiring device 104. The scanning apparatus 102 is connected to a computer system 105 via a universal serial bus (USB) port (not shown). The dual power mode apparatus 100 includes a detection module 106, a switch unit 110, and a power controller 114. The detection module 106 is connected to an external power source via a connection port (not shown). The external power source provides dual power mode apparatus 100 with the first voltage signal. The computer system 105 provides the detection module 106 with a second voltage signal via the universal serial bus (USB) port. Further, the computer system 105 transmits the USB signal to the power controller 114. The switch unit 110 is coupled to the detection module 106 and the power controller 114. The power controller 114 is coupled to the image acquiring device 104.

While the dual power mode apparatus 100 is operated, the detection module 106 receives the first voltage signal and the second voltage signal, or only receives the first voltage signal. The detection module 106 then detects the levels of the first voltage signal and the second voltage signal respectively for generating a detecting signal. The switch unit 110 switches the first voltage signal and the second voltage signal for selection. The power controller 114 receives the detecting signal and the universal serial bus (USB) signal, wherein the universal serial bus (USB) signal further comprises a control signal, data signal and the second voltage signal. The power controller 114 determines whether the first voltage signal is detected according to the detecting signal. The power controller 114 controls the switch unit 110 to activate the switch unit 110 to output the first voltage signal for driving an image acquiring device 104 when the first voltage signal is detected. In another case, the power controller 114 controls the switch unit 110 to activate the switch unit 110 to output the first voltage signal and the second voltage signal for driving the image acquiring device 104 when the first voltage signal is detected. The switch unit 110 outputs the second voltage signal for driving the image acquiring device 104 when the power controller 114 determines that the first voltage signal does not exist, that is, determines that the first voltage signal is absent. In one embodiment, the computer system 105 controls the power controller 114 so that the power controller 114 is capable of determining whether the first voltage signal is detected according to the detecting signal. Meanwhile, the power controller 114 is used to report the detecting signal to the computer system 105 and sends the control signal from the computer system 105 to switch unit 110. For example, the status associated with the first voltage signal is stored into the configuration descriptor accompanied with the USB signal.

Please refer to FIG. 1. The detection module 106 further continuously detects the status of the first voltage signal. The dual power mode apparatus 100 determines whether the power controller 114 has a control entitlement of the first voltage signal when the status of the first voltage signal is changed. For example, the status of the first voltage signal is changed from high level to low level or from low level to high level. The power controller 114 controls the switch unit 110 to output the first voltage signal, or output the first voltage signal and the second voltage signal to the image acquiring device 104 when the status of the first voltage signal is unchanged.

When the power controller 114 has a control entitlement of the first voltage signal, the power controller 114 is capable of enabling the control entitlement of the first voltage signal. In another case, when the power controller 114 has no the control entitlement of the first voltage signal, the power controller 114 is disabled from the control entitlement of the first voltage signal.

When the control entitlement of the first voltage signal is enabled, the power controller 114 determines whether the universal serial bus (USB) signal is disconnected from the scanning apparatus 102. The power controller 114 transmits a re-connection request to allow a computer system 105 to enumerate the scanning apparatus 102 when the power controller 114 disconnects the universal serial bus (USB) signal from the scanning apparatus 102. The scanning apparatus 102 reports the status of the first voltage signal to the computer system 105 via the power controller 114. The detection module 106 further continuously detects the status of the first voltage signal when the power controller 114 does not disconnect the universal serial bus (USB) signal. The control entitlement of the first voltage signal for the power controller 114 is disabled and the power controller 114 reports the status of the first voltage signal to the computer system 105 when the power controller 114 has no the control entitlement of the first voltage signal.

Specifically, when the power controller 114 determines whether the universal serial bus (USB) signal is disconnected and makes re-connection according to the status of the first voltage signal, an application program operated in the computer system 105 can be utilized to enable or disable the power controller 114. When the power controller 114 enables the control entitlement of the first voltage signal, the power controller 114 disconnects the universal serial bus (USB) signal from the scanning apparatus 102, and the power controller 114 reports the status of the first voltage signal when the computer system 105 re-enumerate the scanning apparatus 102. When the power controller 114 disables the control entitlement of the first voltage signal, the power controller 114 reports the changed status of the first voltage signal to the computer system 105.

In another embodiment, the power controller 114 processes the control signal from the computer system 105 for disconnecting the universal serial bus (USB) signal to enumerate the scanning apparatus 102. Basically, the disconnection step is used to meet the command from the computer system 105 but not associated with the control status of the first voltage signal. Therefore, when the power controller 114 is disabled from the control entitlement of the first voltage signal and the power controller 114 cannot disconnect the universal serial bus (USB) signal. However, the application program in the computer system 105 can control the power controller 114 to perform the disconnection step.

The image acquiring device 104 includes a light source 116, an image sensor 118, a voltage control unit 120 and a driving motor 122. The image sensor 118 is coupled to the light source 116. The voltage control unit 120 is coupled to the detection module 106 and the switch unit 110. The driving motor 122 is coupled to the voltage control unit 120 and the image sensor 118. The light source 116 provides the brightness to illuminate the document pages. The image sensor 118 senses image data of the document pages thereon and outputs the analog signal corresponding to the image data. The voltage control unit 120 converts the first voltage signal and the second voltage signal to a first direct current level and a second direct current level. The driving motor 122 drives the image sensor 118. In one embodiment, the first direct current level is used to drive the image acquiring device 104 at a high speed and the second direct current level is used to drive the image acquiring device 104 at a low speed. The image acquiring device 104 further supplies the first direct current level or the second direct current level to the driving motor 122.

According to the above-mentioned, the present invention provides a scanning apparatus 102 having a dual power mode apparatus 100 for supplying either a universal serial bus (USB) power or an external power source to the scanning apparatus, or supplying both the universal serial bus (USB) power and the external power source to the scanning apparatus 102. Therefore, the scanning apparatus 102 having a dual power mode apparatus 100 is supplied with the universal serial bus (USB) power and/or the external power source for increasing the portability of the scanner and improving the inconvenience due to the lack of power socket mains supply. Moreover, based on the selection of varied voltage signal, the scanning speed, e.g. high scanning speed or low scanning speed, of the scanning apparatus 102 can be adjusted to increase the flexibility of the scanning apparatus 102.

Figure 2:
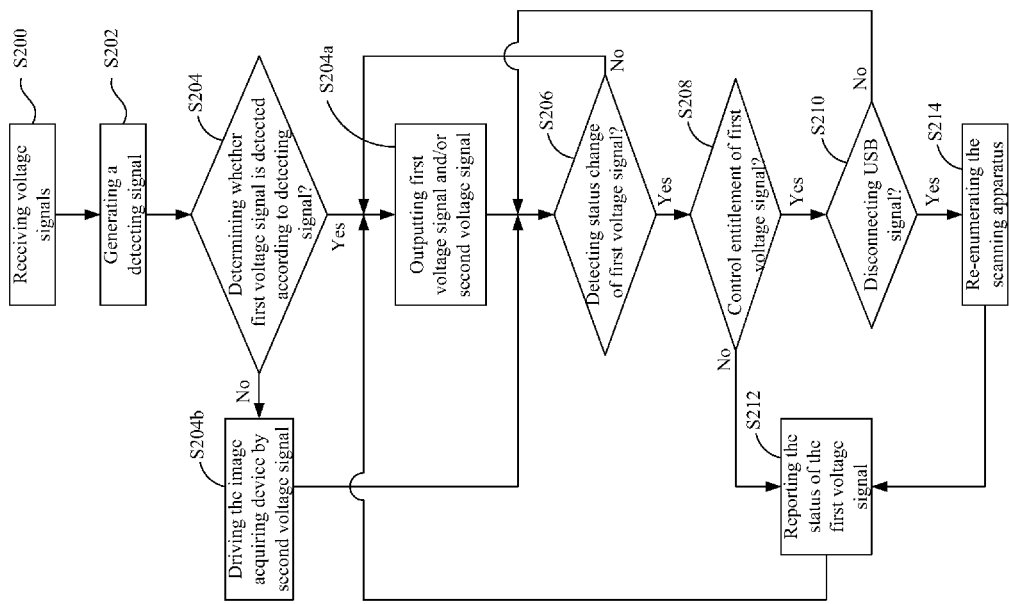
FIG. 2 is a flow chart of scanning method having dual power mode according to one embodiment of the present invention.

Please refer to FIG. 1 and FIG. 2. FIG. 2 is a flow chart of scanning method by a scanning apparatus 102 having dual power mode apparatus 100 according to one embodiment of the present invention. The scanning apparatus 102 includes a dual power mode apparatus 100 and an image acquiring device 104. The dual power mode apparatus 100 includes a detection module 106, a switch unit 110, and a power controller 114. The image acquiring device image 104 includes a light source 116, an image sensor 118, a voltage control unit 120 and a driving motor 122.

In step S200, the detection module 106 receives a first voltage signal and a second voltage signal, or receives the second voltage signal.

In step S202, the detection module 106 detects the levels of the first voltage signal and the second voltage signal respectively for generating a detecting signal.

In step S204, the power controller 114 receives the detecting signal and the universal serial bus (USB) signal, wherein the universal serial bus (USB) signal further includes a control signal and the second voltage signal. The power controller 114 determines whether the first voltage signal is detected according the detecting signal.

As shown in step S204a, the power controller 114 controls the switch unit 110 to activate the switch unit 110 to output the first voltage signal for driving an image acquiring device 104 when the first voltage signal is detected. In another case, the power controller 114 controls the switch unit 110 to activate the switch unit 110 to output the first voltage signal and the second voltage signal for driving the image acquiring device 104 when the first voltage signal is detected. As shown in step S204b, the switch unit 110 outputs the second voltage signal for driving the image acquiring device 104 when the power controller 114 determines that the first voltage signal does not exist. In one embodiment, the computer system 105 controls the power controller 114 so that the power controller 114 is capable of determining whether the first voltage signal is detected according to the detecting signal. Meanwhile, the power controller 114 is used to report the detecting signal to the computer system 105 and sends the control signal from the computer system 105 to switch unit 110. Proceed to step S206.

In step S206, the detection module 106 further continuously detects the status of the first voltage signal. The dual power mode apparatus 100 determines whether the power controller 114 has a control entitlement of the first voltage signal, as shown in step S208, when the status of the first voltage signal is changed. For example, the status of the first voltage signal is changed from high level to low level or from low level to high level. When the status of the first voltage signal is not changed, the step S204a is performed.

In step S208, the dual power mode apparatus 100 determines whether the power controller 114 has a control entitlement of the first voltage signal. When the power controller 114 has a control entitlement of the first voltage signal, the power controller 114 is capable of enabling the control entitlement of the first voltage signal. Proceed to the step S210. In another case, when the power controller 114 has no the control entitlement of the first voltage signal, the power controller 114 is disabled from the control entitlement of the first voltage signal. Return to the step S212.

In step S210, when the control entitlement of the first voltage signal is enabled, the power controller 114 determines whether the universal serial bus (USB) signal is disconnected. The power controller 114 transmits a re-connection request to allow a computer system 105 to re-enumerate the scanning apparatus 102, as shown in S214, when the power controller 114 disconnects the universal serial bus (USB) signal. Return to the step S212 and the scanning apparatus 102 reports the status of the first voltage signal to the computer system 105 via the power controller 114 to indicate the status of the first voltage signal. Return to the step S206 and the detection module 106 further continuously detects the status of the first voltage signal when the power controller 114 does not disconnect the universal serial bus (USB) signal.

In step S212, the control entitlement of the first voltage signal for the power controller 114 is disabled and the power controller 114 reports the status of the first voltage signal to the computer system 105 when the power controller 114 has no the control entitlement of the first voltage signal.

As is understood by a person skilled in the art, the foregoing preferred embodiments of the present invention are illustrative rather than limiting of the present invention. It is intended that they cover various modifications and similar arrangements be included within the spirit and scope of the appended claims, the scope of which should be accorded the broadest interpretation so as to encompass all such modifications and similar structure.

What is claimed is:

1. A dual power mode apparatus for supplying power to a scanning apparatus to scan a plurality of document pages, the dual power mode apparatus comprising:
   a detection module, for receiving a first voltage signal and a second voltage signal of an universal serial bus (USB) signal, wherein the detection module detects the levels of the first voltage signal and the second voltage signal respectively for generating a detecting signal;
   a switch unit coupled to the detection module, for switching the first voltage signal and the second voltage signal; and
   a power controller coupled to the detection module, for receiving the detecting signal, wherein the power controller determines whether the first voltage signal is detected according the detecting signal, and wherein the power controller controls the switch unit to activate the switch unit to output the first voltage signal for driving an image acquiring device when the first voltage signal is detected;
   wherein the power controller determines whether the USB signal is disconnected from the scanning apparatus when the detection module detects the status of the first voltage signal to be changed and the power controller has a control entitlement of the first voltage signal and wherein the power controller transmits a re-connection request to allow a computer system, coupled to the power controller, to enumerate the scanning apparatus when the power controller disconnects the USB signal from the scanning apparatus.

2. The dual power mode apparatus of claim 1, wherein the power controller controls the switch unit to activate the switch unit to output the first voltage signal and the second voltage signal for driving the image acquiring device by the first voltage signal and the second voltage signal.

3. The dual power mode apparatus of claim 1, wherein the switch unit outputs the second voltage signal for driving the image acquiring device when the power controller determines that the first voltage signal does not exist.

4. The dual power mode apparatus of claim 1, wherein the detection module further continuously detects a status of the first voltage signal, and the dual power mode apparatus determines whether the power controller has the control entitlement of the first voltage signal when the status of the first voltage signal is changed.

5. The dual power mode apparatus of claim 4, wherein the control entitlement of the first voltage signal for the power controller is disabled and the power controller reports the status of the first voltage signal to a computer system when the power controller has no the control entitlement of the first voltage signal.

6. The dual power mode apparatus of claim 4, wherein the power controller controls the switch unit to output either the first voltage signal or both the first voltage signal and the second voltage signal to the image acquiring device when the status of the first voltage signal is unchanged.

7. The dual power mode apparatus of claim 1, wherein the scanning apparatus reports the status of the first voltage signal to the computer system via the power controller.

8. A scanning apparatus having a dual power mode, the scanning apparatus comprising:
   a dual power mode apparatus, comprising:
      a detection module, for receiving a first voltage signal and a second voltage signal of an universal serial bus (USB) signal, wherein the detection module detects the levels of the first voltage signal and the second voltage signal respectively for generating a detecting signal;
      a switch unit coupled to the detection module, for switching the first voltage signal and the second voltage signal; and
      a power controller coupled to the detection module, for receiving the detecting signal, wherein the power controller determines whether the first voltage signal is detected according the detecting signal, and wherein the power controller controls the switch unit to activate the switch unit to output the first voltage signal when the first voltage signal is detected;
      wherein the power controller determines whether the USB signal is disconnected from the scanning apparatus when the detection module detects the status of the first voltage signal to be changed and the power controller has a control entitlement of the first voltage signal, and wherein the power controller transmits a re-connection request to allow a computer system, coupled to the power controller, to enumerate the scanning apparatus when the power controller disconnects the USB signal from the scanning apparatus; and
   an image acquiring device coupled to the detection module and the switch unit of the dual power mode apparatus, for receiving the first voltage signal and the second voltage signal for activation.

9. The scanning apparatus of claim 8, wherein the image acquiring device further comprises:
   a light source, for providing brightness to illuminate a plurality of document pages;
   an image sensor coupled to the light source, for sensing image data of the plurality of document pages thereon and outputting analog signal corresponding to the image data;
   a voltage control unit coupled to the detection module and the switch unit, for converting the first voltage signal and the second voltage signal to a first direct current level and a second direct current level; and
   a driving motor coupled to the voltage control unit and the image sensor, for driving the image sensor.

10. The scanning apparatus of claim 8, wherein the power controller controls the switch unit to activate the switch unit to output the first voltage signal and the second voltage signal for driving the image acquiring device by the first voltage signal and the second voltage signal.

11. The scanning apparatus of claim 8, wherein the switch unit outputs the second voltage signal for driving the image acquiring device when the power controller determines that the first voltage signal does not exist.

12. The scanning apparatus of claim 8, wherein the detection module further continuously detects the status of the first voltage signal, and the dual power mode apparatus determines whether the power controller has the control entitlement of the first voltage signal when the status of the first voltage signal is changed.

13. The scanning apparatus of claim 12, wherein the scanning apparatus reports the status of the first voltage signal to the computer system via the power controller.

14. The scanning apparatus of claim 12, wherein the control entitlement of the first voltage signal for the power controller is disabled and the power controller reports the status of the first voltage signal to a computer system when the power controller has no the control entitlement of the first voltage signal.

15. The scanning apparatus of claim 12, wherein the power controller controls the switch unit to output either the first voltage signal or both the first voltage signal and the second voltage signal to the image acquiring device when the status of the first voltage signal is not changed.

* * * * *